United States Patent
Okazaki et al.

(10) Patent No.: US 7,411,095 B2
(45) Date of Patent: Aug. 12, 2008

(54) PROCESS FOR PRODUCTION OF HIGH-PURITY ENAMINES

(75) Inventors: Rei Okazaki, Hiratsuka (JP); Shunshi Kojima, Kamakura (JP); Hideharu Yokokawa, Hiratsuka (JP)

(73) Assignee: Sankyo Company, Limited, Tokyo (JP)

( * ) Notice: Subject to any disclaimer, the term of this patent is extended or adjusted under 35 U.S.C. 154(b) by 377 days.

(21) Appl. No.: 11/037,502

(22) Filed: Jan. 18, 2005

(65) Prior Publication Data

US 2005/0143576 A1  Jun. 30, 2005

Related U.S. Application Data

(63) Continuation of application No. PCT/JP03/09109, filed on Jul. 17, 2003.

(30) Foreign Application Priority Data

Jul. 18, 2002  (JP) ............................. 2002-209623

(51) Int. Cl.
    *C07C 211/00* (2006.01)
(52) U.S. Cl. .................. 564/463; 564/471; 564/478
(58) Field of Classification Search .................. 564/463, 564/471, 478
    See application file for complete search history.

(56) References Cited

U.S. PATENT DOCUMENTS 3,481,939 A  12/1969  Brannock et al.
5,908,858 A  6/1999  Kimura et al.

FOREIGN PATENT DOCUMENTS

EP  799823 A1  10/1997
WO  WO 89/02889 A1  4/1989

OTHER PUBLICATIONS

White et al., Journal of Organic Chemistry, 1967, 32:213-214.*
Barton S.D.; Ollis W.D., "The Synthesis and Reactions of Organic Compounds," *Comprehensive Organic Chemistry*, Editor: Sutherland I.O.; Pergamon, New York, vol. 2, Part 6, 1979.
Maas W., Janssen E., Stamhuis E.J., Wynberg H., "Mechanism of Enamine Reactions, IV.[1a] The Hydrolysis of Tertiary Enamines in Acidic Medium[1b]", *J. Org. Chem.*, vol. 32, pp. 1111-1115, 1967.
Curphey T.J., Hung J.C., Chu C.C.C., "A Study of the Alkylation of Enamines Derived from Sterically Hindered Amines[1]", *J. Org. Chem.*, vol. 40, No. 5, pp. 607-614, 1975.
Sollenberger P.Y., Martin R.B., "Mechanism of Enamine Hydrolysis", *J.Am. Chem.*, vol. 82, pp. 4261-4270, 1970.
Deslongchamps P. et al., "The total synthesis of (+)-ryanodol. Part II. Model studies for rings B and C of (+)-anhydroryanodol. Preparation of a key pentacyclic intermediate", *Can. J. Chem.*, vol. 68, , pp. 127-152, 1990.
Robertson J., Hatley R.J.D., Watkin D.J., "Preparation of the tricyclic ketopyrrole core of roseophilin by radical macrocyclisation and Paal-Knorr condensation", *J. Chem. Soc.*, Perkin Trans. 1, pp. 3389-3396, 2000.

* cited by examiner

*Primary Examiner*—Rei-Tsang Shiao
(74) *Attorney, Agent, or Firm*—Frishauf, Holtz, Goodman & Chick, P.C.

(57) ABSTRACT

A method for producing highly pure enamines, which comprises reacting an aldehyde or ketone with an amine and treating the resulting reaction mixture with an acidic aqueous solution at a temperature between 0° C. and 30° C.

37 Claims, No Drawings

PROCESS FOR PRODUCTION OF HIGH-PURITY ENAMINES

CROSS-REFERENCE TO RELATED APPLICATION

This application is a continuation application of International application PCT/JP2003/009109 filed on Jul. 17, 2003, the entire contents of which are incorporated by reference herein.

FIELD OF THE INVENTION

The present invention relates to a process by which highly pure enamines can be easily produced.

BACKGROUND ART

Enamine is a general term for αβ-unsaturated amines, which are extremely useful compounds in the field of synthetic organic chemistry. Enamines are generally synthesized by a dehydrative condensation reaction between an aldehyde or ketone and a secondary amine. In the synthesis of enamines, the dehydrative condensation reaction has been well known to proceed more smoothly when one equivalent of an aldehyde or ketone is reacted with more than one equivalent of a secondary amine than when one equivalent of an aldehyde or ketone is reacted with one equivalent of a secondary amine. Accordingly, when the excess amount of the secondary amine is used in said synthetic reaction, the desired product, the enamine, and the secondary amine are included in the final product obtained after the reaction is completed. Enamines thus obtained can be used for other reactions without any purifications, but in some reactions, for example, such as a condensation reaction between an enamine and a halogenated alkyl compound, purification of the enamine is necessary because the secondary amine inhibits the reaction. As a procedure for the purification of enamines, fractional distillation is generally known, but especially in the production of a large amount of enamine, large scale fractional distillation equipment is required, and additionally, this purification procedure is generally accompanied by disadvantages such as the decomposition of the enamines in the course of the fractional distillation at a high temperature. Furthermore, it is known that enamines generally have poor stability against water [Barton S. D.; Ollis W. D. Comprehensive Organic Chemistry; Sutherland I. O. Ed.; Pergamon: New York, 1979; Vol. 2, Part 6], and studies on the rate (mechanism) of hydrolysis of various enamines have been reported [J. Org. Chem., 32, 1111 (1967); J. Org. Chem., vol. 40, No. 5, 607-614 (1975); J. Am. Chem. Soc., 82, 4261-4270 (1970), etc.].

SUMMARY OF THE INVENTION

The present inventors have eagerly investigated methods of producing highly pure enamines and found that the enamines obtained using specific secondary amines are unexpectedly stable against water and, additionally, that the highly pure enamines can be easily obtained by a simple treatment using water (an acidic aqueous solution), to complete the present invention.

The present invention relates to:

(1) a method of producing a highly pure compound having the general formula (3)

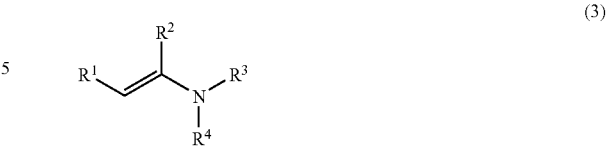

(wherein, $R^1$ and $R^2$ are the same or different and each represents a hydrogen atom, a $C_1$-$C_6$ alkyl group, a $C_1$-$C_6$ alkyl group substituted with substituent(s) selected from the group consisting of Substituent group α and Substituent group β, a $C_6$-$C_{14}$ aryl group, a $C_6$-$C_{14}$ aryl group substituted with substituent(s) selected from Substituent group α, a 5- to 7-membered heteroaryl group containing 1 to 3 sulfur atoms, oxygen atoms and/or nitrogen atoms, or a 5- to 7-membered heteroaryl group containing 1 to 3 sulfur atoms, oxygen atoms and/or nitrogen atoms which is substituted with substituent(s) selected from Substituent group α, or $R^1$ and $R^2$ together form a $C_1$-$C_6$ alkylene group, $R^3$ and $R^4$ are the same or different and each represents a $C_1$-$C_6$ alkyl group, a $C_1$-$C_6$ alkyl group substituted with a $C_1$-$C_6$ alkoxy group or a $C_3$-$C_6$ cycloalkyl group, Substituent group α consists of hydroxyl groups, nitro groups, cyano groups, halogen atoms, $C_1$-$C_6$ alkyl groups, $C_1$-$C_6$ alkoxy groups, $C_1$-$C_6$ alkylthio groups and di($C_1$-$C_6$ alkyl)amino groups, and Substituent group β consists of $C_6$-$C_{14}$ aryl groups, $C_6$-$C_{14}$ aryl groups substituted with substituent(s) selected from Substituent group α, 5- to 7-membered heteroaryl groups containing 1 to 3 sulfur atom, oxygen atom and/or nitrogen atom, and 5- to 7-membered heteroaryl groups containing from 1 to 3 sulfur atoms, oxygen atoms and/or nitrogen atoms which is substituted with substituent(s) selected from Substituent group α), which comprises a step of reacting a compound having the general formula (1)

(wherein, $R^1$ and $R^2$ have the same meanings as those indicated hereinbefore) with a compound having the general formula (2)

$$R^3—(NH)—R^4 \qquad (2)$$

(wherein, $R^3$ and $R^4$ have the same meanings as those indicated hereinbefore) and a step of treating the resulting reaction mixture with an acidic aqueous solution at between 0° C. and 30° C.

Of the method described above, the preferred methods are as follows:

(2) a method wherein $R^1$ is a $C_1$-$C_6$ alkyl group, a $C_1$-$C_6$ alkyl group substituted with substituent(s) selected from Substituent group α and Substituent group β, a $C_6$-$C_{14}$ aryl group, or a $C_6$-$C_{14}$ aryl group substituted with substituent(s) selected from Substituent group α, or $R^1$ and $R^2$ together form a $C_1$-$C_6$ alkylene group, (3) a method wherein $R^1$ is a $C_1$-$C_6$ alkyl group, a $C_1$-$C_6$ alkyl group substituted with substituent(s) selected from Substituent group α and Substituent group β, a $C_6$-$C_{14}$ aryl group, or a $C_6$-$C_{14}$ aryl group substituted with substituent(s) selected from Substituent group α, (4) a method wherein $R^1$ is a $C_1$-$C_4$ alkyl group; a $C_1$-$C_4$ alkyl group substituted with a hydroxyl group, a fluorine atom, a chlorine atom, a methoxy group or a phenyl group; a phenyl group; a naphthyl group; or a phenyl group substituted with a fluorine atom, a chlorine atom, a methyl group or a methoxy group, (5) a method wherein $R^1$ is a methyl, propyl or benzyl group, (6) a method wherein $R^2$ is a hydrogen atom, a $C_1$-$C_6$ alkyl group or a $C_1$-$C_6$ alkyl group substituted with substituent(s) selected from Substituent group α and Substituent group β, (7) a method wherein $R^2$ is a hydrogen atom or a $C_1$-$C_4$ alkyl group, (8) a method wherein $R^2$ is a hydrogen atom, (9) a method wherein $R^3$ and $R^4$ are the same or different and each represents a $C_2$-$C_5$ alkyl group, a $C_2$-$C_5$ alkyl group substituted with a $C_1$-$C_4$ alkoxy group, or a $C_4$-$C_6$ cycloalkyl group,

(10) a method wherein $R^3$ and $R^4$ are the same or different and each represents an isopropyl, isobutyl, isopentyl, 2-methoxyethyl, 3-methoxypropyl, 2-ethoxyethyl, cyclopentyl or cyclohexyl group,

(11) a method wherein each of $R^3$ and $R^4$ is an isobutyl group,

(12) a method wherein the pH of the acidic aqueous solution is between 2 and 6,

(13) a method wherein the acidic aqueous solution is a dilute aqueous solution of a mineral acid selected from dilute sulfuric acid, dilute hydrochloric acid and dilute nitric acid, or an aqueous solution of an organic acid selected from an aqueous solution of acetic acid and aqueous solutions of oxalic acid, carbonic acid, citric acid and phosphoric acid,

(14) a method wherein the acidic aqueous solution is dilute sulfuric acid or an aqueous solution of acetic acid,

(15) a method wherein the concentration of the aqueous solution of mineral acid is between 1 and 15 w/v % and the concentration of the aqueous solution of organic acid is between 3 and 20 w/v %,

(16) a method wherein the concentration of the aqueous solution of mineral acid is between 5 and 10 w/v % and the concentration of the aqueous solution of organic acid is between 5 and 15 w/v %,

(17) a method wherein the concentration of the aqueous solution of mineral acid is between 6 and 8 w/v % and the concentration of the aqueous solution of organic acid is between 8 and 10 w/v %,

(18) a method wherein the temperature of the treatment with an acidic aqueous solution is between 0° C. and 15° C.,

(19) a method wherein the temperature of the treatment with an acidic aqueous solution is between 0° C. and 5° C.,

(20) a method which is characterized by using a dehydrating agent in the step to react the compound having the general formula (1) with the compound having the general formula (2) and by treating the reaction mixture with water at between 0° C. and 30° C. after the completion of the reaction and prior to the treatment using an acidic aqueous solution,

(21) a method wherein the dehydrating agent is magnesium sulfate, potassium carbonate or calcium chloride,

(22) a method wherein the temperature of the treatment with water is between 0° C. and 15° C.,

(23) a method wherein the temperature of the treatment with water is between 0° C. and 5° C.,

(24) a method which is characterized by carrying out the treatment with an acidic aqueous solution followed by treatment with a basic aqueous solution,

(25) a method wherein the pH of the basic aqueous solution is between 13 and 14,

(26) a method wherein the basic aqueous solution is 0.1 to 10 w/v % of an aqueous solution of alkali metal hydroxide, an aqueous solution of alkaline earth metal hydroxide or an aqueous solution of a carbonate salt,

(27) a method wherein the basic aqueous solution is 0.3 to 5 w/v % of an aqueous solution of alkali metal hydroxide, an aqueous solution of alkaline earth metal hydroxide or an aqueous solution of a carbonate salt,

(28) a method wherein the basic aqueous solution is 0.5 to 3 w/v % of an aqueous solution of alkali metal hydroxide, an aqueous solution of alkaline earth metal hydroxide or an aqueous solution of a carbonate salt,

(29) a method wherein the alkali metal hydroxide is sodium hydroxide or potassium hydroxide, the alkaline earth metal hydroxide is calcium hydroxide or barium hydroxide, and the carbonate salt is sodium hydrogencarbonate or calcium carbonate,

(30) a method wherein the temperature of the treatment with a basic aqueous solution is between 0° C. and 30° C.,

(31) a method wherein the temperature of the treatment with a basic aqueous solution is between 0° C. and 15° C., and

(32) a method wherein the temperature of the treatment with a basic aqueous solution is between 0° C. and 5° C.

Furthermore, the present invention relates to

(33) a method of producing a highly pure compound having the general formula (3)

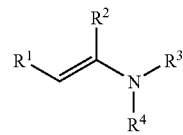

(3)

(wherein, $R^1$ and $R^2$ are the same or different and each represents a hydrogen atom, a $C_1$-$C_6$ alkyl group, a $C_1$-$C_6$ alkyl group substituted with substituent(s) selected from the group consisting of Substituent group α and Substituent group β, a $C_6$-$C_{14}$ aryl group, a $C_6$-$C_{14}$ aryl group substituted with substituent(s) selected from Substituent group α, a 5- to 7-membered heteroaryl group containing 1 to 3 sulfur atoms, oxygen atoms and/or nitrogen atoms, or a 5- to 7-membered heteroaryl group containing 1 to 3 sulfur atoms, oxygen atoms and/or nitrogen atoms which is substituted with substituent(s) selected from Substituent group α, or $R^1$ and $R^2$ together form a $C_1$-$C_6$ alkylene group, $R^3$ and $R^4$ are the same or different and each represents a $C_1$-$C_6$ alkyl group, a $C_1$-$C_6$ alkyl group substituted with a $C_1$-$C_6$ alkoxy group or a $C_3$-$C_6$ cycloalkyl group, Substituent group α consists of hydroxyl groups, nitro groups, cyano groups, halogen atoms, $C_1$-$C_6$ alkyl groups, $C_1$-$C_6$ alkoxy groups, $C_1$-$C_6$ alkylthio groups and di($C_1$-$C_6$ alkyl)amino groups, and Substituent group β consists of $C_6$-$C_{14}$ aryl groups, $C_6$-$C_{14}$ aryl groups substituted with substituent(s) selected from Substituent group α, 5- to 7-membered heteroaryl groups containing 1 to 3 sulfur atoms, oxygen atoms and/or nitrogen atoms, and 5- to 7-membered heteroaryl groups containing from 1 to 3 sulfur atoms, oxygen atoms and/or nitrogen atoms which is substituted with substituent(s) selected from Substituent group α), which comprises a step of reacting a compound having the general formula (1)

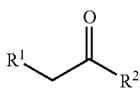

(wherein, $R^1$ and $R^2$ have the same meanings as those indicated hereinbefore) with a compound having the general formula (2)

(wherein, $R^3$ and $R^4$ have the same meanings as those indicated hereinbefore) in the presence of a dehydrating agent, and a step of treating the resulting reaction mixture with water at between 0° C. and 30° C.

Of the synthetic method described above, preferred methods are

(34) a method wherein the temperature of treatment with a basic aqueous solution is between 0° C. and 30° C.,
(35) a method wherein the temperature of treatment with a basic aqueous solution is between 0° C. and 15° C., and
(36) a method wherein the temperature of treatment with a basic aqueous solution is between 0° C. and 5° C.

DETAILED DESCRIPTION OF THE INVENTION

In general formulae (1), (2), and (3), the "$C_1$-$C_6$ alkyl group" in the definition of $R^1$, $R^2$, $R^3$, $R^4$ and Substituent group α; the alkyl moiety of the "$C_1$-$C_6$ alkyl group substituted with substituent(s) selected from Substituent group α and Substituent β" group in the definition of $R^1$ and $R^2$; the alkyl moiety of the "di($C_1$-$C_6$ alkyl)amino group" in the definition of Substituent group α; and the alkyl moiety of the "$C_1$-$C_6$ alkyl group substituted with a $C_1$-$C_6$ alkoxy group" in the definition of $R^3$ and $R^4$ can be a straight or branched chain alkyl group such as a methyl, ethyl, propyl, isopropyl, butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group; as to $R^1$, $R^2$, and Substituent group α, a straight or branched chain $C_1$-$C_4$ alkyl group is preferred, a methyl, ethyl, propyl, isopropyl or butyl group is more preferred, and a methyl, ethyl or propyl group is particularly preferred. As to $R^3$ and $R^4$, a straight or branched chain $C_3$-$C_5$ alkyl group is preferred, a propyl, isopropyl, butyl, isobutyl or isopentyl group is more preferred, an isopropyl, isobutyl or isopentyl group is particularly preferred, and an isobutyl group is most preferred.

The "$C_1$-$C_6$ alkyl group substituted with substituent(s) selected from Substituent group α and Substituent group β" in the definition of $R^1$ and $R^2$ is preferably a $C_1$-$C_6$ alkyl group substituted with from 1 to 5 substituents selected from Substituent group α and Substituent group β, and more preferably a $C_1$-$C_6$ alkyl group substituted with from 1 to 3 substituents selected from Substituent group α and Substituent group β.

The "$C_6$-$C_{14}$ aryl group" and the aryl moiety of the "$C_6$-$C_{14}$ aryl group substituted with substituent(s) selected from Substituent group β" in the definition of $R^1$, $R^2$ and Substituent group β can be, for example, a phenyl, naphthyl, phenanthryl or anthracenyl group, and is preferably a phenyl or naphthyl group and most preferably a phenyl group.

Further, the "$C_6$-$C_{14}$ aryl group" described above may optionally be fused with a $C_3$-$C_{10}$ cycloalkyl group (preferably a $C_5$-$C_6$ cycloalkyl group), and such a fused aryl group is, for example, a 5-indanyl group.

The "$C_6$-$C_{14}$ aryl group substituted with substituent(s) selected from Substituent group α" in the definition of $R^1$, $R^2$ and Substituent group β is preferably a $C_6$-$C_{14}$ aryl group substituted with from 1 to 4 substituents selected from Substituent group α, preferably a $C_6$-$C_{14}$ aryl group substituted with from 1 to 3 substituents selected from Substituent group α, and still more preferably a $C_6$-$C_{14}$ aryl group substituted with from 1 to 3 substituents selected from the group consisting of fluorine atoms, chlorine atoms, methyl, ethyl, methoxy and ethoxy groups.

The "5- to 7-membered heteroaryl group containing from 1 to 3 sulfur atoms, oxygen atoms and/or nitrogen atoms" and the "5- to 7-membered heteroaryl group containing from 1 to 3 sulfur atoms, oxygen atoms and/or nitrogen atoms" moiety of the "5- to 7-membered heteroaryl group containing from 1 to 3 sulfur atoms, oxygen atoms and/or nitrogen atoms which is substituted with substituent(s) selected from Substituent group α" in the definition of $R^1$, $R^2$ and Substituent group β can be, for example, a furyl, thienyl, pyrrolyl, pyrazolyl, imidazolyl, oxazolyl, isoxazolyl, thiazolyl, isothiazolyl, triazolyl, thiadiazolyl, pyridyl, pyridazinyl, pyrimidinyl, pyrazinyl or azepinyl group, and is preferably a 5- to 6-membered heteroaryl group containing from 1 to 2 sulfur atoms, oxygen atoms and/or nitrogen atoms such as a furyl, thienyl, pyrrolyl, pyrazolyl, imidazolyl, oxazolyl, isoxazolyl, thiazolyl, isothiazolyl, pyridyl, pyridazinyl, pyrimidinyl or pyrazinyl group, and more preferably a pyridyl or pyrimidinyl group.

Further, the "5- to 7-membered heteroaryl group containing from 1 to 3 sulfur atoms, oxygen atoms and/or nitrogen atoms" described above may optionally be fused with other cyclic groups [for example, a $C_6$-$C_{14}$ aryl group (preferably a $C_6$-$C_{10}$ aryl group) or a $C_3$-$C_{10}$ cycloalkyl group (preferably a $C_5$-$C_6$ cycloalkyl group)], and such a fused heteroaryl group can be, for example, an indolyl, benzofuranyl, benzothienyl, quinolyl, isoquinolyl, quinazolinyl, tetrahydroquinolyl or tetrahydroisoquinolyl group.

The "5- to 7-membered heteroaryl group containing from 1 to 3 sulfur atoms, oxygen atoms and/or nitrogen atoms which is substituted with substituent(s) selected from Substituent group α" in the definition of $R^1$, $R^2$ and Substituent group β is preferably a 5- to 7-membered heteroaryl group containing from 1 to 3 sulfur atoms, oxygen atoms and/or nitrogen atoms which is substituted with from 1 to 3 substituents selected from Substituent group α, more preferably a 5- to 7-membered heteroaryl group containing from 1 to 3 sulfur atoms, oxygen atoms and/or nitrogen atoms which is substituted with from 1 to 2 substituents selected from Substituent group α, and still more preferably a 5- to 7-membered heteroaryl group containing from 1 to 3 sulfur atoms, oxygen atoms and/or nitrogen atoms which is substituted with from 1 to 2 substituents selected from the group consisting of fluorine atoms, chlorine atoms, methyl, ethyl, methoxy and ethoxy groups.

The "$C_1$-$C_6$ alkylene group" formed together with $R^1$ and $R^2$ can be a straight or branched chain alkylene group such as a methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene or hexamethylene group, and is preferably a straight or branched chain $C_2$-$C_5$ alkylene group, more preferably a straight chain $C_3$-$C_4$ alkylene group, still more preferably a trimethylene or tetramethylene group, and most preferably a tetramethylene group.

The "$C_1$-$C_6$ alkoxy group" in the definition of Substituent group α, and the alkoxy moiety of the "$C_1$-$C_6$ alkyl group substituted with a $C_1$-$C_6$ alkoxy group" in the definition of $R^3$ and $R^4$ is a group wherein an oxygen atom is bonded to the "$C_1$-$C_6$ alkyl group" described above, and preferably is a straight or branched chain $C_1$-$C_4$ alkoxy group, more preferably a methoxy, ethoxy, propoxy, isopropoxy or butoxy group, and particularly preferably a methoxy, ethoxy or propoxy group.

The "$C_1$-$C_6$ alkyl group substituted with a $C_1$-$C_6$ alkoxy group" in the definition of $R^3$ and $R^4$ is preferably a $C_2$-$C_5$ alkyl group substituted with a $C_1$-$C_4$ alkoxy group, more preferably an ethyl, propyl, isopropyl, n-butyl, isobutyl or isopentyl group, each of which is substituted with a methoxy, ethoxy or propoxy group, and still more preferably a 2-methoxyethyl, 3-methoxypropyl or 2-ethoxyethyl group.

The "$C_3$-$C_6$ cycloalkyl group" in the definition of $R^3$ and $R^4$ can be a cyclopropyl, cyclobutyl, cyclopentyl or cyclohexyl group, and is preferably a $C_4$-$C_6$ cycloalkyl group, and more preferably a cyclopentyl or cyclohexyl group.

The "halogen atom" in the definition of Substituent group α is a fluorine atom, chlorine atom, bromine atom or iodine atom, and preferably a fluorine atom or chlorine atom.

The "$C_1$-$C_6$ alkylthio group" in the definition of Substituent group α is a group wherein a sulfur atom is bonded to the "$C_1$-$C_6$ alkyl group" described above, and is preferably a straight or branched chain $C_1$-$C_4$ alkylthio group, more preferably a methylthio, ethylthio, propylthio, isopropylthio or butylthio group, and particularly preferably a methylthio, ethylthio or propylthio group.

For $R^1$, $R^2$, $R^3$, and $R^4$, the preferred groups are as follows.

$R^1$ is preferably a $C_1$-$C_6$ alkyl group, a $C_1$-$C_6$ alkyl group substituted with substituent(s) selected from Substituent group α and Substituent group β, a $C_6$-$C_{14}$ aryl group or a $C_6$-$C_{14}$ aryl group substituted with substituent(s) selected from Substituent group α, or $R^1$ forms, together with $R^2$, a $C_1$-$C_6$ alkylene group; more preferably a $C_1$-$C_6$ alkyl group or a $C_1$-$C_6$ alkyl group substituted with substituent(s) selected from Substituent group α and Substituent group β; still more preferably a $C_1$-$C_4$ alkyl group, a $C_1$-$C_4$ alkyl group substituted with a hydroxyl group, fluorine atom, chlorine atom, methoxy or phenyl group, a phenyl group, a naphthyl group, or a phenyl group substituted with a fluorine atom, chlorine atom; methyl group or methoxy group; and particularly preferably a methyl, propyl or benzyl group.

$R^2$ is preferably a hydrogen atom, a $C_1$-$C_6$ alkyl group or a $C_1$-$C_6$ alkyl group substituted with substituent(s) selected from Substituent group α and Substituent group β; more preferably a hydrogen atom or a $C_1$-$C_4$ alkyl group; and particularly preferably a hydrogen atom.

$R^3$ and $R^4$ are preferably the same or different and each is a $C_2$-$C_5$ alkyl group, a $C_2$-$C_5$ alkyl group substituted with a $C_1$-$C_4$ alkoxy group, or a $C_4$-$C_6$ cycloalkyl group; more preferably an isopropyl, isobutyl, isopentyl, 2-methoxyethyl, 3-methoxypropyl, 2-ethoxyethyl, cyclopentyl or cyclohexyl group, and particularly preferably an isobutyl group.

The Substituent group α preferably consists of hydroxyl groups, nitro groups, cyano groups, halogen atoms, $C_1$-$C_4$ alkyl groups, $C_1$-$C_4$ alkoxy groups, $C_1$-$C_4$ alkylthio groups and di($C_1$-$C_4$ alkyl)amino groups: more preferably hydroxyl groups, fluorine atoms, chlorine atoms and methyl, ethyl, methoxy, ethoxy, methylthio and dimethylamino groups; and particularly preferably fluorine atom, chlorine atoms, and methyl, ethyl, methoxy and ethoxy groups.

The Substituent group β preferably consists of $C_6$-$C_{14}$ aryl groups and $C_6$-$C_{14}$ aryl groups substituted with substituent(s) selected from Substituent group α; more preferably $C_6$-$C_{10}$ aryl groups and $C_6$-$C_{10}$ aryl groups substituted with from 1 to 3 substituents selected from Substituent group α; and more preferably phenyl groups and phenyl groups substituted with from 1 to 3 substituents selected from the group consisting of fluorine atoms, chlorine atoms and methyl, ethyl, methoxy and ethoxy groups.

In the present invention, "highly pure" means that the purity is 80% or more (preferably 90% or more, and more preferably 95% or more), and the purity can be, for example, confirmed by calculation of peak area ratio using gas chromatography.

The reaction to produce the compound of the general formula (3) by reacting a compound of the general formula (1) with a compound of general formula (2) is performed according to commonly known methods to produce enamines [for example, U.S. Pat. No. 3,481,939; Can. J. Chem. Vol. 68, 127-152 (1990); J. Chem. Soc., Perkin Trans. 1, 3389-3396 (2000); etc.].

<Method to Remove Excess Amine (the Compound of the General Formula (2)) from the Reaction Mixture>

When more than one equivalent of the compound of the general formula (2) shown above is reacted with one equivalent of the compound of general formula (1) shown above, the compound of general formula (3) shown above and the compound of general formula (2) are contained in the reaction mixture. The compound of general formula (2) remaining in the reaction mixture can be easily removed by a treatment with an acidic aqueous solution, that is, by adding an acidic aqueous solution to the reaction mixture, shaking or stirring it for from 5 minutes to 2 hours and, then, removing the aqueous layer.

The acidic aqueous solution to be employed can be, for example, a dilute aqueous solution of mineral acid such as dilute sulfuric acid, dilute hydrochloric acid or dilute nitric acid, or an aqueous solution of organic acid such as an aqueous solution of acetic acid, and aqueous solutions of oxalic acid, carbonic acid, citric acid and phosphoric acid, and is preferably dilute sulfuric acid or an aqueous solution of acetic acid. Specifically, in the case of an aqueous solution of a mineral acid, 1 to 15 w/v % (preferably 5 to 10 w/v %, and more preferably between 6 and 8 w/v %) of such a solution can be used, while in the case of an aqueous solution of an organic acid, 3 to 20 w/v % (preferably 5 to 15 w/v %, and more preferably 8 to 10 w/v %) of such an aqueous solution can be used. Generally, an acidic aqueous solution with a pH value of between 1 and 7 (preferably between 2 and 6) can be used.

The addition of an acidic aqueous solution and shaking or stirring can be performed at 0° C. to 30° C. (preferably at 0° C. to 15° C., and more preferably at 0° C. to 5° C.).

Furthermore, when the molecular weight of the enamine is large, some of them are in the form of solid or have a low fluidity at the treatment temperature mentioned above. In these cases, said treatment can be performed after the addition of a water-insoluble aprotic solvent such as N,N-dimethylformamide, N,N-dimethylacetamide, dimethylsulfoxide, benzene, toluene or hexane to the reaction mixture.

After the treatment of the reaction mixture with the acidic aqueous solution in the manner mentioned above, if necessary, it can be furthermore treated with a basic aqueous solution.

The basic aqueous solution to be employed is not particularly restricted, provided that it does not decompose the produced enamines, and can be, for example, a dilute aqueous solution of an alkali metal hydroxide such as a dilute aqueous solution of sodium hydroxide or a dilute aqueous solution of potassium hydroxide; a dilute aqueous solution of an alkaline earth metal hydroxide such as a dilute aqueous solution of calcium hydroxide; or an aqueous solution of a carbonate salt such as an aqueous solution of sodium hydrogencarbonate or an aqueous solution of calcium carbonate, and is preferably a dilute aqueous solution of sodium hydroxide or a dilute aqueous solution of potassium hydroxide. Specifically, 0.1 to 10 w/v % (preferably 0.3 to 5 w/v %, and more preferably 0.5 to 3 w/v %) of such an aqueous solution can be used. Generally, a basic aqueous solution with a pH value of between 7 and 14 (preferably between 13 and 14) can be used.

The "treating with using a basic aqueous solution" means the addition of the basic aqueous solution and shaking or stirring of the resulting mixture for from 5 minutes to 2 hours, and can be performed at 0° C. to 30° C. (preferably at 0° C. to 15° C., and more preferably at 0° C. to 5° C.).

Furthermore, when the molecular weight of the enamine is large, some of them are in the form of a solid or have a low fluidity at the treatment temperature mentioned above. In these cases, said treatment can be performed after the addition of a water-insoluble aprotic solvent such as N,N-dimethylformamide, N,N-dimethylacetamide, dimethylsulfoxide, benzene, toluene or hexane to the reaction mixture.

<Method to Remove the Dehydrating Agent from the Reaction Mixture>

In the case that a compound of the general formula (1) shown above is reacted with a compound of the general formula (2) shown above in the presence of a dehydrating agent and the dehydrating agent is removed from the reaction mixure after the completion of the reaction, said dehydrating agent can be easily removed by treatment with water, that is, by adding sufficient water (or ice water) to dissolve the dehydrating agent, shaking or stirring it for from 5 minutes to 2 hours and, then, removing the aqueous layer.

The dehydrating agent to be employed in this case is not particularly restricted, provided that it can generally be used as a dehydrating agent for the production of enamines and that it dissolves in water, and can be, for example, magnesium sulfate, sodium sulfate, potassium carbonate, calcium carbonate or calcium chloride, and preferably magnesium sulfate.

The addition of water (ice water) and shaking or stirring can be performed at 0° C. to 30° C. (preferably at 0° C. to 15° C., and more preferably at 0° C. to 5° C.).

Furthermore, when the molecular weight of the enamine is large, some of them are in the form of solid or have a low fluidity at the treatment temperature mentioned above. In these cases, said treatment can be performed after the addition of a water-insoluble aprotic solvent such as N,N-dimethylformamide, N,N-dimethylacetamide, dimethylsulfoxide, benzene, toluene or hexane to the reaction mixture.

The present invention will hereinafter be described in more detail by way of the Examples, but the scope of the present invention should not be limited to these examples.

EXAMPLES

Example 1

N,N-Bis(2-methylpropyl)-1-propenylamine

To a suspension of magnesium sulfate (15.1 g) in diisobutylamine (107.3 g) was added dropwise propionaldehyde (24.8 g) at 0-10° C. under a nitrogen atmosphere, and it was stirred at 10-15° C. for 1.5 hours. After ice-cooling, water (90 ml) was added and it was stirred to dissolve the magnesium sulfate. After the removal of the aqueous layer, to the organic layer obtained was added an 8% (w/v) aqueous sulfuric acid solution (300 ml) at 0-5° C. and then stirred for 10 minutes. The aqueous layer was, then, removed again, a 0.5% (w/v) aqueous sodium hydroxide solution (90 ml) was added to the organic layer at 0-5° C., and stirred for 10 minutes. After stirring, the aqueous layer was removed to afford the title compound (57.0 g, yield: 76%, purity: 96.7%) as a colorless oil.

$^1$H-NMR spectrum (400 MHz, CDCl$_3$) δ ppm: 0.84 (d, J=6.6 Hz, 12H), 1.61 (d,J=6.3 Hz, 3H), 1.83-1.93 (m, 2H), 2.67 (d, J=7.3 Hz, 4H), 3.92-4.00 (m, 1H), 5.90 (d,J=13.8 Hz, 1H).

Example 2

N,N-Bis(2-methylpropyl)-1-propenylamine

To a suspension of magnesium sulfate (10.1 g) in diisobutylamine (72.2 g) was added dropwise propionaldehyde (16.4 g) at 0-10° C. under a nitrogen atmosphere, and it was stirred at 10-15° C. for 1.5 hours. After ice-cooling, water (60 ml) was added and it was stirred to dissolve the magnesium sulfate. After the removal of the aqueous layer, to the organic layer obtained was added a 9% (w/v) aqueous acetic acid solution (200 ml) at 0-5° C. and then stirred for 10 minutes. The aqueous layer was, then, removed again, a 0.5% (w/v) aqueous sodium hydroxide solution (60 ml) was added to the organic layer at 0-5° C., and stirred for 5 minutes. After stirring, the aqueous layer was removed to afford the title compound (42.5 g, yield: 81%, purity: 95.3%) as a colorless oil.

The $^1$H-NMR spectrum of the compound obtained was substantially identical to that of Example 1.

Example 3

N,N-Bis(2-methylpropyl)-pentanylamine

To a suspension of magnesium sulfate (10.1 g) in diisobutylamine (72.0 g) was added dropwise valeraldehyde (24.6 g) at 0-5° C. under a nitrogen atmosphere, and it was stirred at 10-15° C. for 1 hour. After ice-cooling, water (60 ml) was added and it was stirred to dissolve the magnesium sulfate. After the removal of the aqueous layer, to the organic layer obtained was added a 9% (w/v) aqueous acetic acid solution (200 ml) at 0-5° C. and then stirred for 5 minutes. The aqueous layer was, then, removed again, a 0.5% (w/v) aqueous sodium hydroxide solution (60 ml) was added to the organic layer at 0-5° C., and stirred for 5 minutes. After stirring, the aqueous layer was removed to afford the title compound (51.3 g, yield: 80%, purity: 93.8%) as a colorless oil.

$^1$H-NMR spectrum (400 MHz, CDCl$_3$) δ ppm: 0.84 (d, J=6.6 Hz, 12H), 0.86 (t, J=7.3 Hz, 3H), 1.26-1.35 (m, 2H), 1.83-1.94 (m, 2H), 2.68 (d, J=7.3 Hz, 4H), 3.93-4.00 (m, 1H), 5.88 (d, J=13.7 Hz, 1H).

According to the present invention, highly pure enamines can be easily produced.

What is claimed is:

1. A method of producing a highly pure compound having a formula (3)

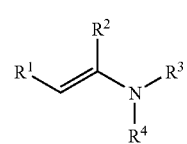

(3)

wherein $R^1$ and $R^2$ are the same or different and each represents a hydrogen atom, an unsubstituted $C_1$-$C_6$ alkyl group, a $C_1$-$C_6$ alkyl group substituted with at least one substituent selected from the group consisting of a Substituent group α and a Substituent group β, an unsubstituted $C_6$-$C_{14}$ aryl group or a $C_6$-$C_{14}$ aryl group substituted with at least one substituent from Substituent group α, $R^3$ and $R^4$ are the same or different and each represents an unsubstituted $C_1$-$C_6$ alkyl group, a $C_1$-$C_6$ alkyl group substituted with a $C_1$-$C_6$ alkoxy group or a $C_3$-$C_6$ cycloalkyl group, Substituent group α is selected from the group consisting of a hydroxyl group, a nitro group, a cyano group, a halogen atom, a $C_1$-$C_6$ alkyl group, a $C_1$-$C_6$ alkoxy group, a $C_1$-$C_6$ alkylthio group and a di($C_1$-$C_6$ alkyl) amino group, and Substituent group β is selected from the group consisting of an unsubstituted $C_6$-$C_{14}$ aryl group and a $C_6$-$C_{14}$ aryl group substituted with at least one substituent from Substituent group α, which comprises (a) reacting a compound having a formula (1)

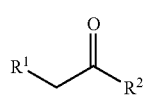  (1)

wherein $R^1$ and $R^2$ have the same meanings as those indicated hereinbefore, with a compound having a formula (2)

  (2)

wherein $R^3$ and $R^4$ have the same meanings as those indicated hereinbefore, wherein the compound of the formula (2) is in an amount which is more than one equivalent of the compound of the formula (1), (b) treating the resulting reaction mixture from step (a) with an acidic aqueous solution selected from the group consisting of a dilute aqueous solution of mineral acid and an aqueous solution of an organic acid, at a temperature between 0° C. and 30° C. and (c) carrying out a treatment on the resulting reaction mixture from step (b) with a basic aqueous solution.

2. The method according to claim 1, wherein $R^1$ is an unsubstituted $C_1$-$C_6$ alkyl group, a $C_1$-$C_6$ alkyl group substituted with at least one substituent selected from the group consisting of Substituent group α and Substituent group β, an unsubstituted $C_6$-$C_{14}$ aryl group, or a $C_6$-$C_{14}$ aryl group substituted with at least one substituent from Substituent group α.

3. The method according to claim 1, wherein $R^1$ is an unsubstituted $C_1$-$C_6$ alkyl group, a $C_1$-$C_6$ alkyl group substituted with at least one substituent selected from the group consisting of Substituent group α and Substituent group β, an unsubstituted $C_6$-$C_{14}$ aryl group, or a $C_6$-$C_{14}$ aryl group substituted with at least one substituent from Substituent group α.

4. The method according to claim 1, wherein $R^1$ is an unsubstituted $C_1$-$C_4$ alkyl group; a $C_1$-$C_4$ alkyl group substituted with a hydroxyl group, a fluorine atom, a chlorine atom, a methoxy or a phenyl group; an unsubstituted phenyl group; a naphthyl group; or a phenyl group substituted with a fluorine atom, a chlorine atom, a methyl group or a methoxy group.

5. The method according to claim 1, wherein $R^1$ is a methyl group, a propyl group or a benzyl group.

6. The method according to any one of claims 1 to 5, wherein $R^2$ is a hydrogen atom, an unsubstituted $C_1$-$C_6$ alkyl group or a $C_1$-$C_6$ alkyl group substituted with at least one substituent selected from the group consisting of Substituent group α and Substituent group β.

7. The method according to any one of claims 1 to 5, wherein $R^2$ is a hydrogen atom or a $C_1$-$C_4$ alkyl group.

8. The method according to any one of claims 1 to 5, wherein $R^2$ is a hydrogen atom.

9. The method according to claim 1, wherein $R^3$ and $R^4$ are the same or different and each represents an unsubstituted $C_2$-$C_5$ alkyl group, a $C_2$-$C_5$ alkyl group substituted with a $C_1$-$C_4$ alkoxy group, or a $C_4$-$C_6$ cycloalkyl group.

10. The method according to claim 1, wherein $R^3$ and $R^4$ are the same or different and each represents an isopropyl group, an isobutyl group, an isopentyl group, a 2-methoxyethyl group, a 3-methoxypropyl group, a 2-ethoxyethyl group, a cyclopentyl group or a cyclohexyl group.

11. The method according to claim 1, wherein $R^3$ and $R^4$ are an isobutyl group.

12. The method according to claim 1, wherein the acidic aqueous solution has a pH between 2 and 6.

13. The method according to claim 1, wherein the acidic aqueous solution is selected from the group consisting of a dilute sulfuric acid, a dilute hydrochloric acid, a dilute nitric acid, an aqueous solution of acetic acid, an aqueous solution of oxalic acid, an aqueous solution of carbonic acid, an aqueous solution of citric acid and an aqueous solution of phosphoric acid.

14. The method according to claim 13, wherein the acidic aqueous solution is a dilute sulfuric acid or an aqueous solution of acetic acid.

15. The method according to claim 13 or claim 14, wherein the aqueous solution is the aqueous solution of the mineral acid and has a concentration between 1 and 15 w/v %; or is the aqueous solution of the organic acid and has a concentration between 3 and 20 w/v %.

16. The method according to claim 13 or claim 14, wherein the aqueous solution is the aqueous solution of the mineral acid and has a concentration between 5 and 10 w/v %; or is the aqueous solution of the organic acid and has a concentration between 5 and 15 w/v %.

17. The method according to claim 13 or claim 14, wherein the aqueous solution is the aqueous solution of the mineral acid and has a concentration between 6 and 8 w/v %; or is the aqueous solution of the organic acid and has a concentration between 8 to 10 w/v %.

18. The method according to claim 1, wherein the temperature of the treating with the acidic aqueous solution is between 0° C. and 15° C.

19. The method according to claim 1, wherein the temperature of the treating with the acidic aqueous solution is between 0° C. and 5° C.

20. The method according to claim 1, further comprising introducing a dehydrating agent in step (a); and treating the resultant reaction mixture in step (b) with water at a temperature between 0° C. and 30° C. after the completion of the reaction and prior to the treating with the acidic aqueous solution.

21. The method according to claim 20, wherein the dehydrating agent is magnesium sulfate, potassium carbonate or calcium chloride.

22. The method according to claim 20, wherein the treating with water is carried out at a temperature between 20° C. and 15° C.

23. The method according to claim 20, wherein the treating with water is carried out at a temperature between 0° C. and 5° C.

24. The method according to claim 1, wherein the basic aqueous solution has a pH between 13 and 14.

25. The method according to claim 1, wherein the basic aqueous solution has a concentration of 0.1 to 10 w/v % and is selected from the group consisting of an aqueous solution of an alkali metal hydroxide, an aqueous solution of an alkaline earth metal hydroxide and an aqueous solution of a carbonate salt.

26. The method according to claim 25, wherein the basic aqueous solution has a concentration of 0.3 to 5 w/v % and is selected from the group consisting of an aqueous solution of an alkali metal hydroxide, an aqueous solution of an alkaline earth metal hydroxide and an aqueous solution of a carbonate salt.

27. The method according to claim 25, wherein the basic aqueous solution has a concentration of 0.5 to 3 w/v % and is selected from the group consisting of an aqueous solution of an alkali metal hydroxide, an aqueous solution of an alkaline earth metal hydroxide and an aqueous solution of a carbonate salt.

28. The method according to any one of claims 24 to 27, wherein the alkali metal hydroxide is sodium hydroxide or potassium hydroxide; the alkaline earth metal hydroxide is calcium hydroxide or barium hydroxide; and the carbonate salt is sodium hydrogencarbonate or calcium carbonate.

29. The method according to claim 1, wherein the treatment with the basic aqueous solution is carried out at a temperature between 0° C. and 30° C.

30. The method according to claim 1, wherein the treatment with the basic aqueous solution is carried out at a temperature between 0° C. and 15° C.

31. The method according to claim 1, wherein the treatment with the basic aqueous solution is carried out at a temperature between 0° C. and 5° C.

32. A method of producing a highly pure compound having a formula (3)

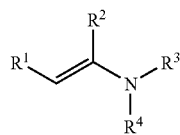

(3)

wherein $R^1$ and $R^2$ are the same or different and each represents a hydrogen atom, an unsubstituted $C_1$-$C_6$ alkyl group, a $C_1$-$C_6$ alkyl group substituted with at least one substituent selected from the group consisting of a Substituent group α and a Substituent group β, an unsubstituted $C_6$-$C_{14}$ aryl group or a $C_6$-$C_{14}$ aryl group substituted with at least one substituent from Substituent group α, $R^3$ and $R^4$ are the same or different and each represents an unsubstituted $C_1$-$C_6$ alkyl group, a $C_1$-$C_6$ alkyl group substituted with a $C_1$-$C_6$ alkoxy group or a $C_3$-$C_6$ cycloalkyl group, Substituent group α is selected from the group consisting of a hydroxyl group, a nitro group, a cyano group, a halogen atom, a $C_1$-$C_6$ alkyl group, a $C_1$-$C_6$ alkoxy group, a $C_1$-$C_6$ alkylthio group and a di($C_1$-$C_6$ alkyl) amino groups, and Substituent group β is selected from the group consisting of an unsubstituted $C_6$-$C_{14}$ aryl group and a $C_6$-$C_{14}$ aryl group substituted with at least one substituent from Substituent group α, which comprises (a) reacting a compound having a formula (1)

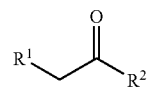

(1)

wherein $R^1$ and $R^2$ have the same meanings as those indicated hereinbefore, with a compound having a formula (2)

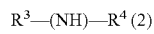

$R^3$—(NH)—$R^4$ (2)

wherein $R^3$ and $R^4$ have the same meanings as those indicated hereinbefore, in the presence of a dehydrating agent, and (b) treating the resulting reaction mixture from step (a) with water at a temperature between 0° C. and 30° C.

33. The method according to claim 32, further comprising after step (b), carrying out a treatment with an acidic aqueous solution and, then, a treatment with a basic aqueous solution.

34. The method according to claim 33, wherein the temperature of treatment with the basic aqueous solution is carried out at a temperature between 0° C. and 30° C.

35. The method according to claim 33, wherein the temperature of treatment with the basic aqueous solution is carried out at a temperature between 0° C. and 15° C.

36. The method according to claim 33, wherein the temperature of treatment with the basic aqueous solution is carried out at a temperature between 0° C. and 5° C.

37. The method according to claim 1, wherein the compound of formula (3) is N,N-bis(2-methylpropyl)-1-propenylamine.

* * * * *